United States Patent
Haywood et al.

[19]

[11] Patent Number: 5,849,015
[45] Date of Patent: Dec. 15, 1998

[54] ORTHOPAEDIC STEM INSERTER WITH QUICK RELEASE LEVER AND RATCHET

[75] Inventors: Bill H. Haywood, Warsaw; Billie W. McBroom, Milford; William C. Smith, Columbia City; Scott J. Steffensmeier; William F. Warrender, Jr., both of Warsaw, all of Ind.; David J. Krueger, Austin, Tex.

[73] Assignee: Bristol-Myers Squibb Company, New York, N.Y.

[21] Appl. No.: 927,715

[22] Filed: Sep. 11, 1997

[51] Int. Cl.$^6$ ........................................ A61B 17/56
[52] U.S. Cl. ................................................ 606/99
[58] Field of Search ............................... 606/99, 100, 86, 606/85, 84

[56] References Cited

U.S. PATENT DOCUMENTS

| | | |
|---|---|---|
| 3,857,389 | 12/1974 | Amstutz . |
| 4,676,798 | 6/1987 | Noiles . |
| 4,686,971 | 8/1987 | Harris et al. . |
| 4,993,410 | 2/1991 | Kimsey . |
| 5,064,427 | 11/1991 | Burkinshaw . |
| 5,133,765 | 7/1992 | Cuilleron . |
| 5,391,170 | 2/1995 | McGuire et al. . |
| 5,443,471 | 8/1995 | Swajger . |
| 5,476,466 | 12/1995 | Barrette et al. . |
| 5,499,986 | 3/1996 | Dimarco . |
| 5,514,136 | 5/1996 | Richelsoph . |

FOREIGN PATENT DOCUMENTS

| | | |
|---|---|---|
| 0 207 873 B1 | 1/1987 | European Pat. Off. . |
| 0 408 109 A1 | 1/1991 | European Pat. Off. . |
| WO 94/05211 | 3/1994 | WIPO . |

OTHER PUBLICATIONS

Linvatec Concept Arthroscopy—Paramax™ Angled Driver–catalog p. 79–1992.
Osteonics–C–Taper Head Dissassembly—Head Disassembly Instrument–1992.
Smith & Nephew Richards—Modular Hip System–Femoral Head Removal Device–1991.
Zimmer, Inc.—Humeral Stem Driver–Fenlin Shoulder Surgical Technique, p. 2–1989.
Zimmer, Inc.—Humeral Stem Inserter—Fenlin Shoulder Surgical Technique, p. 3–c1994–Lit No. 97–4065–102 Rev 2.
Zimmer, Inc.—Fenlin Total Shoulder brochure–c1993–Literature No. 97–4065–101, Rev. 3.
Zimmer, Inc.—Femoral Pros. Holder and Femoral Neck Punch–catalog pp. A13, A41–Jun. 1978.
Zimmer, Inc.—Inserting and Disassembly Instruments–Zimmer catalog p. A87–1991.

*Primary Examiner*—Guy V. Tucker
*Attorney, Agent, or Firm*—Margaret L. Geringer

[57] ABSTRACT

An orthopaedic stem inserter grips and inserts a prosthetic implant having a stem into a prepared opening in a bone. A handle includes a housing, a rotating knob connected to a first end of the housing, and an elongate element connected to the knob and extending through the housing to a second end of the housing. A body includes a pair of jaws, with each jaw being configured to grip the implant. One of the jaws is movable in directions toward and away from the other jaw. A geared rack is connected with the movable jaw. A first gear is connected with the rack, and a second gear is connected with the elongate element and selectively enmeshes with the first gear. A quick release lever is pivotally attached to the handle and has an engaging portion which engages the second gear. The quick release lever moves the second gear toward and away from the first gear upon pivotal movement relative to the handle and thereby respectively enmeshes and demeshes the first and second gears. A ratchet device allows movement of the movable jaw in the direction toward the other jaw upon application of an external force to the movable jaw.

21 Claims, 3 Drawing Sheets

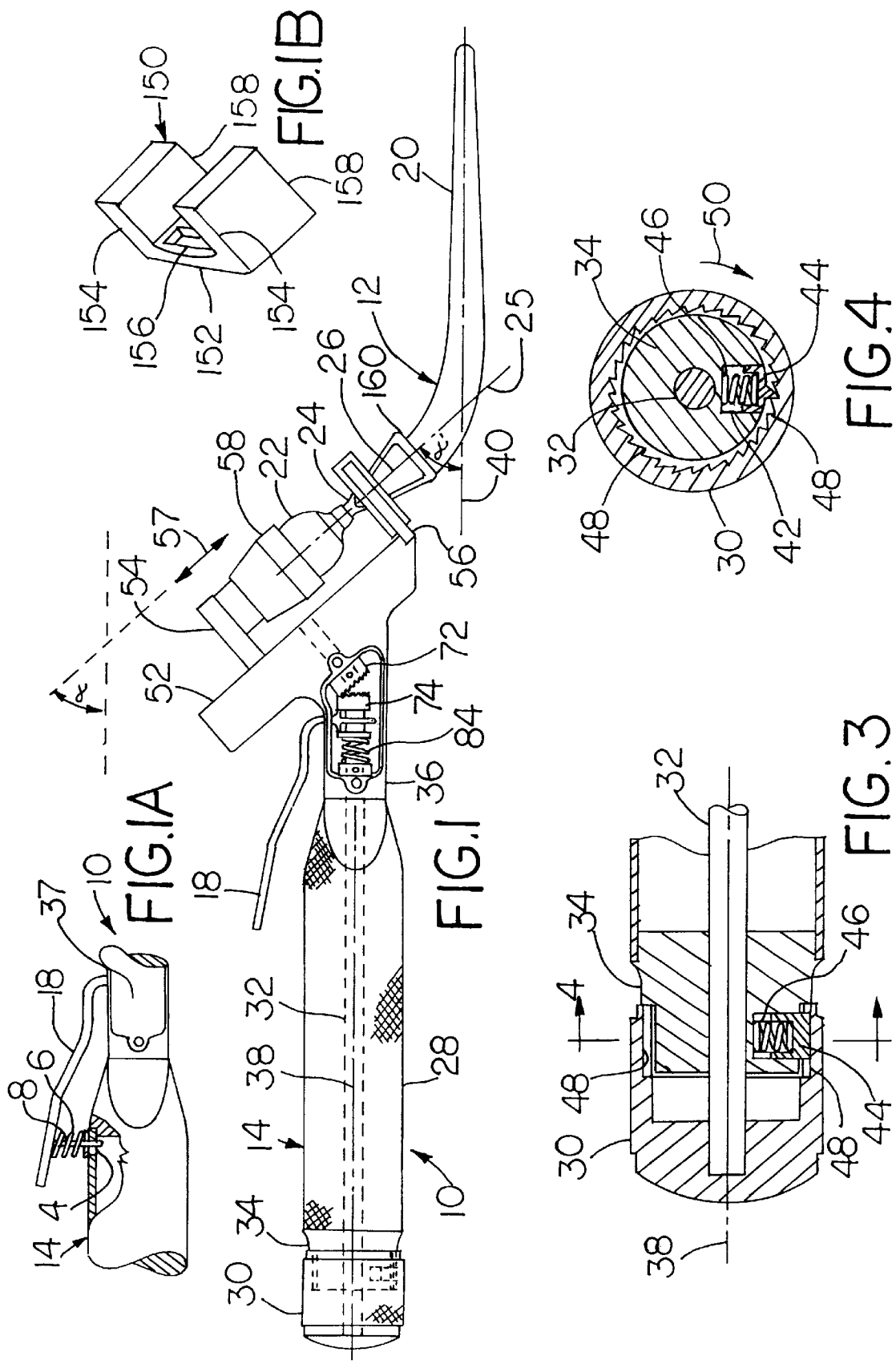

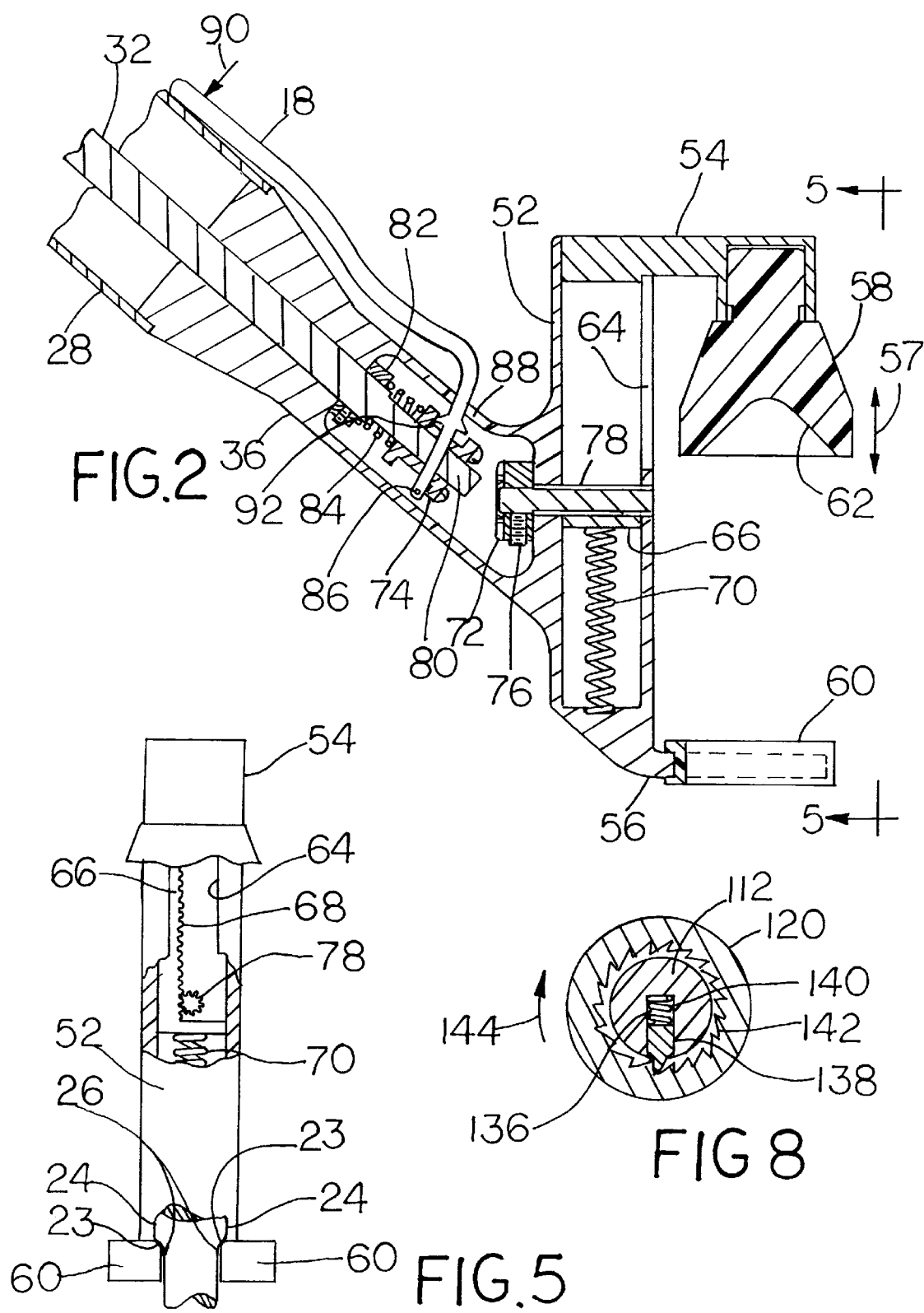

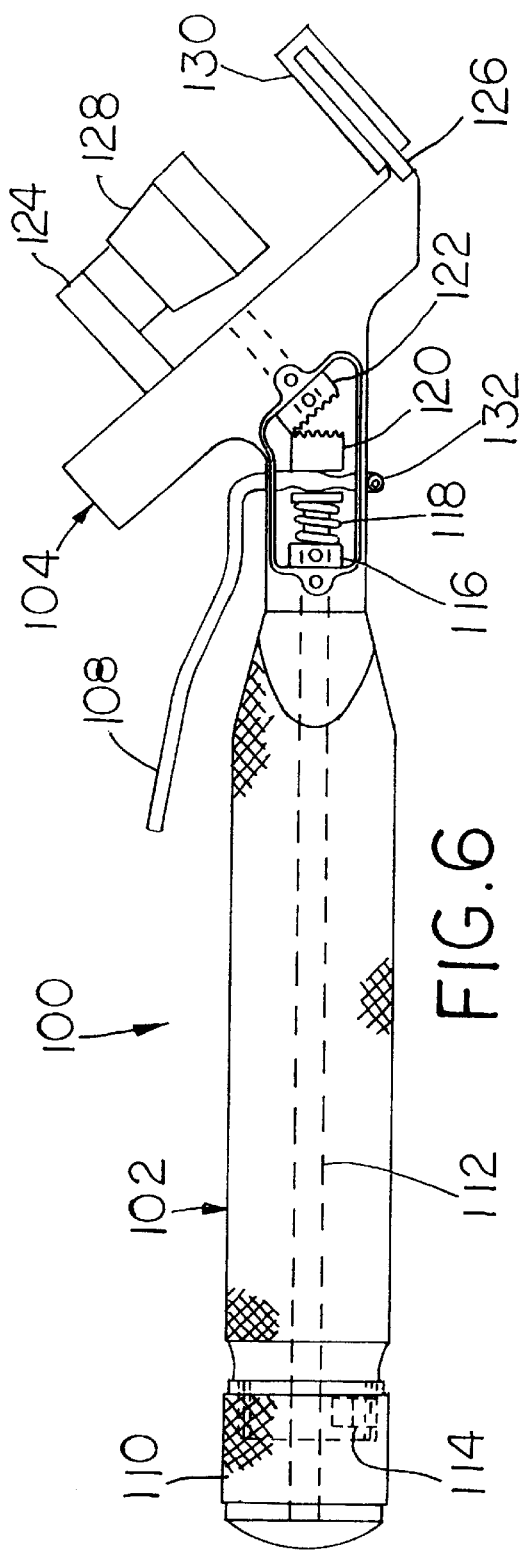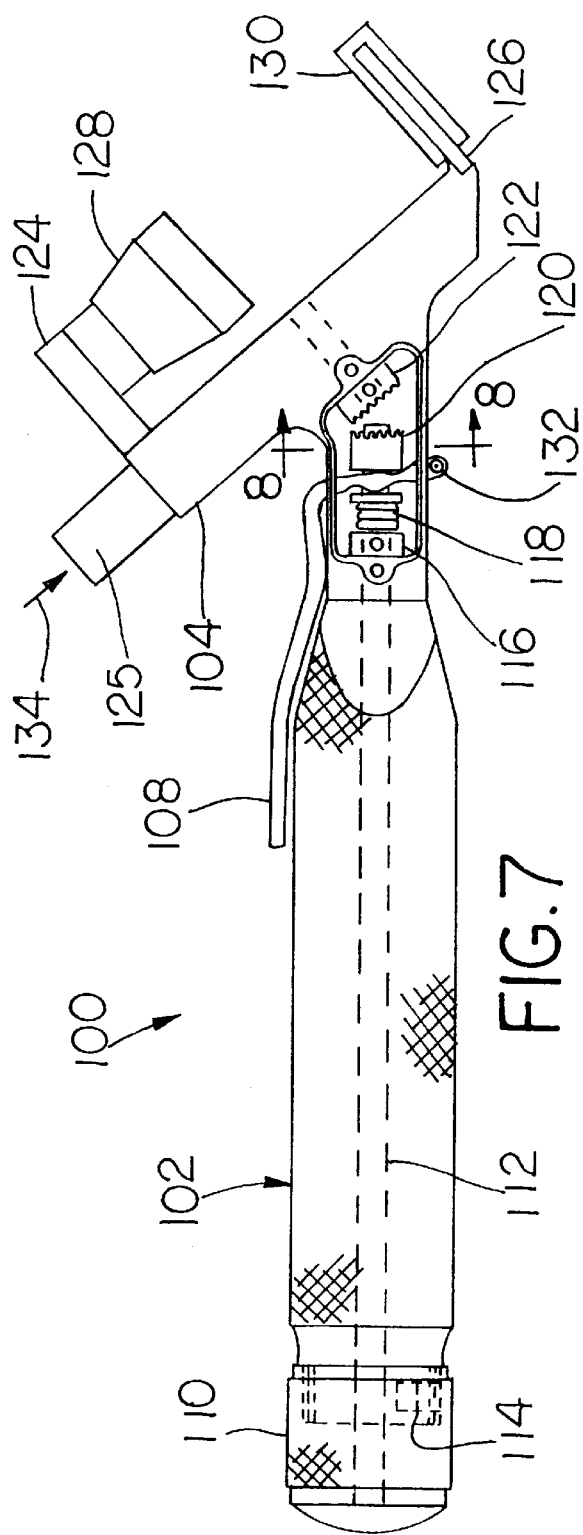

ORTHOPAEDIC STEM INSERTER WITH QUICK RELEASE LEVER AND RATCHET

BACKGROUND OF THE INVENTION

1. Field of the invention.

The present invention relates to orthopaedic instrumentation for use with orthopaedic implants, and, more particularly, to a stem inserter for gripping and inserting an orthopaedic implant having a stem.

2. Description of the related art.

Orthopaedic instrumentation for use with prosthetic implants generally may be used to prepare a bone for receiving the implant, positioning the implant relative to the prepared bone, inserting the implant into the prepared bone and/or extracting the implant from the bone. A stem inserter for use with a prosthetic implant having a stem is used to position the implant relative to a prepared opening in the bone and insert the implant in the prepared opening.

For example, a prosthetic implant in the form of a femoral component includes a stem at the distal end thereof and a head at the proximal end thereof, or a neck at the proximal end thereof for receiving a femoral head. More particularly, the femoral component may include an opening which is formed therein at a position between the head and the stem. The stem inserter may include a transverse locator post which is slid into the transverse opening in the femoral component. The stem inserter is then clamped to a top shoulder of the femoral component such that the femoral component may be positioned within a prepared opening in a femur. An example of such a stem inserter is disclosed in U.S. Pat. No. 5,476,466 (Barrette, et al.), which is assigned to the assignee of the present invention.

SUMMARY OF THE INVENTION

The present invention provides an orthopaedic stem inserter having a body with a pair of jaws, one of which is movable in opposing directions toward and away from another jaw and transverse to a longitudinal axis of a handle; a quick release lever allowing the movable jaw to move quickly away from the other jaw; and a ratchet device allowing the movable jaw to be moved toward the other jaw upon application of an external force to the movable jaw.

The invention comprises, in one form thereof, an orthopaedic stem inserter for gripping and inserting a prosthetic implant having a stem into a prepared opening in a bone. A handle includes a housing, a rotating knob connected to a first end of the housing, and an elongate element connected to the knob and extending through the housing to a second end of the housing. A body includes a pair of jaws, with each jaw being configured to grip the implant. One of the jaws is movable in directions toward and away from the other jaw. A geared rack is connected with the movable jaw. A first gear is connected with the rack, and a second gear is connected with the elongate element and selectively enmeshes with the first gear. A quick release lever is pivotally attached to the handle and has an engaging portion which engages the second gear. The quick release lever moves the second gear toward and away from the first gear upon pivotal movement relative to the handle and thereby respectively enmeshes and demeshes the first and second gears. A ratchet device allows movement of the movable jaw in the direction toward the other jaw upon application of an external force to the movable jaw.

An advantage of the present invention is that a ratchet device is provided to allow the jaws to be quickly and easily attached to the prosthetic implant.

Another advantage of the present invention is that a quick release lever is provided to allow the jaws to be quickly and easily detached from the prosthetic implant without jarring the implant upon release.

Yet another advantage of the present invention is that the jaws are oriented along an axis which is transverse to the longitudinal axis of the handle such that an engaged stem is positioned substantially parallel to the longitudinal axis of the handle, thereby allowing the stem to be more easily visually aligned with the prepared opening in the bone.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 1 is a perspective view of an embodiment of an orthopaedic stem inserter of the present invention, shown connected with a prosthetic implant in the form of a femoral component;

FIG. 1A is a fragmentary, side view in partial cross-section of the stem inserter of FIG. 1 showing an optional spring between the lever and the handle;

FIG. 1B is a perspective view of an optional insertion stop adaptor;

FIG. 2 is a fragmentary, side sectional view of the stem inserter of FIG. 1, with the quick release lever depressed;

FIG. 3 is a fragmentary, side sectional view of the rotating knob at the end of the handle of the stem inserter of FIG. 1;

FIG. 4 is a sectional view of the rotating knob, taken along line 4—4 in FIG. 3;

FIG. 5 is a fragmentary, sectional view of the body, taken along line 5—5 in FIG. 2, with a fragmentary portion of the femoral component positioned in the fixed jaw;

FIG. 6 is a side view of another embodiment of an orthopaedic stem inserter of the present invention, with the quick release lever in a non-depressed position;

FIG. 7 is a side view of the stem inserter of FIG. 6, with the quick release lever in a depressed position; and FIG. 8 is a sectional view of the second gear and associated ratchet device, taken along line 8—8 in FIG. 7.

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Referring now to the drawings, and more particularly to FIGS. 1–5, there is shown an embodiment of an orthopaedic stem inserter 10 of the present invention. Stem inserter 10 may be connected with a prosthetic implant in the form of a femoral component 12. Stem inserter 10 generally includes a handle 14, body 52 and quick release lever 18.

Femoral component 12 includes a stem 20 which may be inserted into a prepared opening in a femur (not shown). A femoral head 22 is connected with a neck 24 of femoral component 12. A recessed area 26 is disposed between neck 24 and stem 20, on each side of femoral component 12 (FIGS. 1 and 5), which creates a shoulder 23 at the top of each recessed area 26.

Handle 14 includes a housing 28, a rotating knob 30 and an elongate element 32. Rotating knob 30 is connected to a first end 34 of housing 28. In the embodiment shown, elongate element 32 is in the form of a cylindrical rod. Elongate element 32 passes through first end 34 of housing 28 and is rigidly connected with rotating knob 30. Elongate element 32 is disposed within and extends through housing 28 to a second end 36, generally opposite from first end 34. Elongate element 32 has a longitudinal axis which is substantially coincident with the longitudinal axis of cylindrical housing 28, both of which are commonly referenced as axis 38 in FIGS. 1 and 3. Moreover, longitudinal axis 38 of elongate element 32 and housing 28 is disposed substantially parallel to the longitudinal axis 40 associated with stem 20. This parallel relationship between housing 28 and stem 20 allows femoral component 12 to be more easily positioned relative to a prepared opening in a bone (not shown).

Referring now to FIG. 4, a first ratchet device allows rotating knob 30 to be rotated in one direction about the longitudinal axis 38 of housing 28, while preventing rotation of knob 30 in an opposing direction about longitudinal axis 38. More particularly, handle 28 includes an opening 42 which is formed in first end 34. A beveled ratchet tooth 44 is disposed within opening 42, and is biased in a direction out of opening 42 via a compression spring 46. Ratchet tooth 44 engages one of a plurality of internal teeth 48 formed at the interior diameter of knob 30. Knob 30 can thus rotate in one direction relative to first end 34, as indicated by directional arrow 50. On the other hand, ratchet tooth 44 prevents rotation of knob 30 relative to first end 34 in a rotational direction which is opposite to arrow 50.

Body 52 which carries a pair of jaws 54 and 56 which are used for gripping femoral component 12. Movable jaw 54 is movable in opposing directions toward and away from fixed jaw 56, as indicated by double headed arrow 57. The opposing directions indicated by arrow 57 are transverse to the longitudinal axis 38 of elongate element 32. In the embodiment shown, the movable jaw 54 is movable in opposing directions 57 which are disposed at an acute angle α relative to longitudinal axis 38. This angle α preferable corresponds to the angle α' between axis 40 of stem 20 and the longitudinal axis 25 of the neck 24. Thus, angle α and α' are preferably substantially the same. An elastomeric cup 58 is carried by movable jaw 54; and an elastomeric pad 60 is carried by fixed jaw 56. Cup 58 includes a recessed surface 62 which engages the top of femoral head 22. Recessed surface 62 may be concave or conical or any other suitable shape. In addition, surface 62 could be shaped to engage the femoral neck 24, if it is desired to grip the femoral component 12 without the head 22 attached. Pad 60 has a generally U-shaped configuration, with each leg engaging a corresponding recessed area 26 on femoral component 12 (FIGS. 1 and 5).

Body 52 has a generally cylindrical shape in the embodiment shown in FIGS. 1–5. A cutout 64 (FIGS. 2 and 5) in body 52 allows movable jaw 54 to move in opposing directions 57 relative to body 52. Movable jaw 54 includes a rack 66 having a plurality of teeth 68. Rack 66 is slidable within the cylindrical opening formed in body 52, and is biased in a direction out of the opening formed in body 52 by a compression spring 70.

An interconnecting device interconnects elongate element 32 with movable jaw 54 at the second end 36 of housing 28. The interconnecting device effects movement of movable jaw 54 upon rotation of knob 30 at first end 34 of housing 28. More particularly, the interconnecting device includes geared rack 66 of movable jaw 54, a first gear 72 connected with rack 66 and a second gear 74 connected with elongate element 32. First gear 72 is connected to a pinion gear 78 via set screw 76 (FIG. 2). Pinion gear 78 in turn enmeshes with rack 66, and thereby connects first gear 72 with rack 66.

Second gear 74 is carried by elongate element 32, and is slidable along a portion of the length of elongate element 32. In the embodiment shown, second gear 74 has a substantially square opening formed therein which is slightly larger than an end 80 of elongate element 32 having a corresponding square cross section. Thus elongate element 32 has a circular cross-section throughout the majority of its length except for end portion 80 which has a square cross-section. End portion 80 also is slightly reduced in width compared to the remainder of elongate portion 32. Second gear 74 is movable between a first position which is enmeshed with first gear 72 (FIG. 1), and a second position which is demeshed with first gear 72 (FIG. 2). A collar 82 is attached to elongate element 32 using, e.g., a set screw, and provides a stop surface facing second gear 74. A compression spring 84 is interposed between second gear 74 and collar 82, and biases second gear 74 toward first gear 72. First and second gears 72 and 74 (FIG. 1) are bevel gears which accommodate the angular relationship of longitudinal axis 38 of handle 14 to body 52 (and thus to the opposing directions 57 of movable jaw 54).

Quick release lever 18 is pivotally attached to handle 14 using a pivot pin 86 located within an interior of housing 28 at second end 36. Quick release lever 18 extends through a slot 88 formed in housing 28 which allows lever 18 to be pivoted between the positions shown in FIGS. 1 and 2. When no force is applied to quick release lever 18, compression spring 84 biases second gear 74 into enmeshed engagement with first gear 72. The end of quick release lever 18 is thus disposed a distance away from housing 28, as shown in FIG. 1. On the other hand, when an external force is applied to quick release lever 18, as shown by arrow 90 in FIG. 2, lever 18 pivots about pivot pin 86 such that the end of lever 18 is disposed closely adjacent to or against housing 28. An engaging portion 92 on quick release lever 18 engages an annular groove cut around the periphery of second gear 74. Moving the end of lever 18 toward housing 28 as indicated by arrow 90 in turn causes engaging portion 92 to move second gear 74 away from first gear 72 and thereby demesh second gear 74 and first gear 72.

In use, recessed area 26 of femoral component 12 is slid into engagement with fixed jaw 56 such that U-shaped elastomeric pad 60 is engaged with the shoulder 23 of each respective recessed area 26. Knob 30 is then rotated, which in turn rotates second gear 74 via the interconnection with elongate element 32. Second gear 74 in turn rotates first gear 72 and pinion gear 78. Rotation of pinion gear 78 causes translational movement of rack 66, thereby causing movable jaw 54 and elastomeric cup 58 to move toward femoral head 22. Knob 30 is rotated until cup 58 firmly engages the top of femoral head 22. Femoral component 12 can then be positioned relative to and inserted within a prepared opening in a femur. To detach stem inserter 10 from femoral component 12, quick release lever 18 is moved toward housing 28, as indicated by arrow 90. This causes second gear 74 to move away from and demesh with first gear 72, thereby allowing compression spring 70 to bias rack 66 and movable jaw 54 away from femoral head 22. Stem inserter 10 may then be detached from femoral component 12 by simply sliding fixed jaw 56 out of engagement with recessed areas 26 on femoral component 12.

FIG. 1A shows an optional compression spring 6 which may be utilized between lever 18 and handle 14. This helps the gears 72, 74 from being accidently disengaged during impaction of inserter 10 upon positioning of femoral component 12. Compression spring 6 is positioned about pin 8 which is fixed to lever 18 and extends through opening 4 in handle 14. Alternatively, the user can place a finger(s) under lever 18 while impacting the instrument to help prevent lever 18 from being permaturely depressed.

FIG. 1B shows an optional insertion stop adaptor 150 which selectively fits over fixed jaw 56 of inserter 10. The adaptor 150 includes a wall 152 with two side arms 154. A window 156 is provided in the upper portion of wall 152 to receive U-shaped fixed jaw 56 and pad 60 therethrough. Adaptor 150 is designed so that the distal surface 158 of arms 154 contacts the calcar bone of the femur upon insertion of the femoral component 12 into the femur, when the femoral component 12 does not include a collar or does not include a collar large enough to contact the calcar bone upon insertion, e.g. as with a minimized collar. The distal surface 158 is designed to align with the level of the cut calcar bone or the bottom of an extending minimized collar, such as 160 on femoral component 12. Various sizes of adaptors 150 may be provided for varying sizes of stems.

Referring now to FIGS. 6-8, there is shown another embodiment of an orthopaedic stem inserter 100 of the present invention. Stem inserter 100 includes many components which are configured similar to the components of stem inserter 10 shown in FIGS. 1-5. For example, stem inserter 100 includes a handle 102, body 104 and quick release lever 108. Moreover, stem inserter 100 includes a knob 110, elongate element 112, first ratchet device 114, collar 116, compression spring 118, second gear 120, first gear 122, movable jaw 124, fixed jaw 126, elastomeric cup 128 and elastomeric pad 130, similar to the respectively named parts making up stem inserter 10 described above. In contrast with stem inserter 10, however, stem inserter 100 includes a quick release lever 108 which is pivotally attached via a pivot pin 132 at a location which is disposed outside of the housing of handle 102. Moreover, body 104 of stem inserter 100 is formed with a substantially square cross section, rather than a circular cross section as defined by body 52 of stem inserter 10.

A more substantive difference between the embodiments of stem inserter 100 and stem inserter 10 is that elongate element 112 of stem inserter 100 has a circular cross-section throughout its length, rather than having a square cross-section portion as with end portion 80 of elongated element 32 of stem inserter 10. Stem inserter 100 also includes a second ratchet device which allows movable jaw 124 to be moved in a direction toward fixed jaw 126 upon application of an external force to movable jaw 124 in a direction toward fixed jaw 126, via jaw extension 125, as indicated by arrow 134 (FIG. 7). The second ratchet device also prevents movement of movable jaw 124 in a direction away from fixed jaw 126 upon application of an external force to movable jaw 124 in a direction away from fixed jaw 126. More particularly, referring to FIG. 8, elongate element 112 includes an opening 136 which extends partially therein. A ratchet tooth 138 is slidably disposed within opening 136, and biased in a direction out of opening 136 by a compression spring 140. Second gear 120 includes a plurality of interior teeth 142 formed at the inside diameter thereof. Ratchet tooth 138 and interior teeth 142 allow second gear 120 to move in a single rotational direction relative to elongate element 112 (indicated by arrow 144), while preventing relative rotational movement between ratchet tooth 138 and interior teeth 142 in a direction opposite to arrow 144. When knob 110 is rotated in a direction such that elongate element 112 rotates in the direction of arrow 144, no relative rotational movement occurs between ratchet tooth 138 and second gear 120, thus rotating second gear 120. On the other hand, when an external force is applied to the end of movable jaw 124, as indicated by arrow 134, the rack associated with movable jaw 134 drives first gear 122 and second gear 120 in the direction of arrow 144, thereby allowing relative movement between second gear 120 and elongate element 112. Thus, movable jaw 124 may be quickly moved into contact with the top of femoral head 22 by pushing movable jaw toward fixed jaw 126. The ratcheting rotational movement between ratchet tooth 138 and second gear 120 allows movable jaw 124 to be relatively easily translated toward fixed jaw 126.

With the exception of the second ratchet device defined in part by ratchet tooth 138 and second gear 120 allowing sliding movement of movable jaw 124 toward fixed jaw 126 upon application of an external force to movable jaw 124, the operation of stem inserter 100 is essentially the same as the operation of stem inserter 10 described above. Accordingly, the operation of stem inserter 100 is not described in further detail.

In the embodiments of stem inserters 10 and 100 shown in the drawings (FIGS. 1,6,7) and described above, the respective handles 14 and 102 are shown with the cover plates removed from the side of the handles at the end connected with respective bodies 52 and 104 for purposes of illustration and description. It will be appreciated that during use, a cover plate such as 37, partially shown in FIG. 1A, is installed to cover the area including first gears, such as 74, and second gears, such as 72.

It is noted that stem inserters 10 and 100 may be made by any suitable manufacturing methods and of any suitable materials. Preferably, the majority of the components of the inserter instrument are made of a suitable metal material, such as stainless steel, except for the cup 58, 128, the pad 60, 130, and the adaptor 150, which are preferably made out of a suitable plastic material.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic stem inserter for gripping and inserting a prosthetic implant having a stem into a prepared opening in a bone, said stem inserter comprising:

a handle including a housing, a rotating knob connected to a first end of said housing, and an elongate element connected to said knob and extending through said housing to a second end of said housing;

a body including a pair of jaws, each said jaw being configured to grip the implant, one of said jaws being movable in directions toward and away from an other of said jaws;

means for interconnecting said elongate element with said movable jaw at said second end of said housing, whereby rotation of said knob at said first end of said housing causes said movement of said movable jaw, said interconnecting means comprising a geared rack connected with said movable jaw, a first gear connected with said rack, and a second gear connected with said elongate element and selectively enmeshing with said first gear;
and
a quick release lever pivotally attached to said handle, said quick release lever having an engaging portion which engages said second gear, said quick release lever moving said second gear toward and away from said first gear upon pivotal movement relative to said handle and thereby respectively enmeshing and demeshing said first and second gears.

2. The orthopaedic stem inserter of claim 1, further comprising a spring engaged with said movable jaw and biasing said movable jaw in said direction away from said other jaw.

3. The orthopaedic stem inserter of claim 1, further comprising a pinion gear connected with said first gear, said first gear being connected with said rack via said pinion gear.

4. The orthopaedic stem inserter of claim 1, wherein said handle and said elongate element have substantially coincident longitudinal axes, and wherein said movable jaw is movable in opposing directions toward and away from said other jaw, said opposing directions being transverse to said longitudinal axis of said elongate element.

5. The orthopaedic stem inserter of claim 4, wherein the longitudinal axis is substantially parallel to a longitudinal axis of the stem.

6. The orthopaedic stem inserter of claim 1, further comprising a ratchet device allowing movement of said movable jaw in said direction toward said other jaw upon application of an external force to said movable jaw in said direction toward said other jaw, said ratchet device preventing movement of said movable jaw in said direction away from said other jaw upon application of an external force to said movable jaw in said direction away from said other jaw.

7. The orthopaedic stem inserter of claim 1, wherein said elongate element comprises a cylindrical rod.

8. The orthopaedic stem inserter of claim 1, wherein one of said jaws is movable in directions toward and away from said other jaw, and said other jaw is fixed.

9. The orthopaedic stem inserter of claim 1, further comprising a spring between the lever and the handle.

10. The orthopaedic stem inserter of claim 1, further comprising an insertion stop adaptor which selectively fits over said other jaw to control the depth that the stem is inserted into the bone.

11. An orthopaedic stem inserter for gripping and inserting a prosthetic implant having a stem into a prepared opening in a bone, said stem inserter comprising:
a handle including a housing, a rotating knob connected to a first end of said housing, and an elongate element connected to said knob and extending through said housing to a second end of said housing;
a body including a pair of jaws, each said jaw being configured to grip the implant, one of said jaws being movable in directions toward and away from an other of said jaws; and
means for interconnecting said elongate element with said movable jaw at said second end of said housing, whereby rotation of said knob at said first end of said housing causes said movement of said movable jaw; and
a ratchet device allowing movement of said movable jaw in said direction toward said other jaw upon application of an external force to said movable jaw in said direction toward said other jaw, said ratchet device preventing movement of said movable jaw in said direction away from said other jaw upon application of an external force to said movable jaw in said direction away from said other jaw.

12. The orthopaedic stem inserter of claim 11, wherein said interconnecting means comprises a geared rack connected with said movable jaw, a first gear connected with said rack, and a second gear connected with said elongate element and enmeshing with said first gear.

13. The orthopaedic stem inserter of claim 12, further comprising a pinion gear connected with said first gear, said first gear being connected with said rack via said pinion gear.

14. The orthopaedic stem inserter of claim 12, wherein said second gear is selectively enmeshed with said first gear.

15. The orthopaedic stem inserter of claim 12, further comprising a quick release lever which is pivotally attached to said handle, said quick release lever having an engaging portion which engages said second gear, said quick release lever moving said second gear toward and away from said first gear upon pivotal movement relative to said handle and thereby respectively enmeshing and demeshing said first and second gears.

16. The orthopaedic stem inserter of claim 11, wherein said handle and said elongate element have substantially coincident longitudinal axes, and wherein said movable jaw is movable in opposing directions toward and away from said other jaw, said opposing directions being transverse to said longitudinal axis of said elongate element.

17. An orthopaedic stem inserter for gripping and inserting a prosthetic implant having a stem into a prepared opening in a bone, said stem inserter comprising:
a handle including a housing, a rotating knob connected to a first end of said housing, and an elongate element connected to said knob and extending through said housing to a second end of said housing, said handle and said elongate element having substantially coincident longitudinal axes;
a body including a pair of jaws, each said jaw being configured to grip the implant, one of said jaws being movable in opposing directions toward and away from an other of said jaws, said opposing directions being transverse to said longitudinal axis of said elongate element; and
means for interconnecting said elongate element with said movable jaw at said second end of said housing, whereby rotation of said knob at said first end of said housing causes said movement of said movable jaw.

18. The orthopaedic stem inserter of claim 17, wherein said interconnecting means comprises a geared rack connected with said movable jaw, a first gear connected with said rack, and a second gear connected with said elongate element and enmeshing with said first gear.

19. The orthopaedic stem inserter of claim 18, further comprising a quick release lever which is pivotally attached to said handle, said quick release lever having an engaging portion which engages said second gear, said quick release lever moving said second gear toward and away from said first gear upon pivotal movement relative to said handle and thereby respectively enmeshing and demeshing said first and second gears.

20. The orthopaedic stem inserter of claim 19, further comprising a ratchet device allowing movement of said movable jaw in said direction toward said other jaw upon application of an external force to said movable jaw in said direction toward said other jaw, said ratchet device preventing movement of said movable jaw in said direction away from said other jaw upon application of an external force to said movable jaw in said direction away from said other jaw.

21. The orthopaedic stem inserter of claim 18, further comprising a pinion gear connected with said first gear, said first gear being connected with said rack via said pinion gear.

* * * * *